US005851819A

United States Patent [19]
Gottesman et al.

[11] Patent Number: 5,851,819
[45] Date of Patent: Dec. 22, 1998

[54] VECTORS CARRYING MDR1 CDNA WHICH CONFER MULTIDRUG RESISTANCE ON TRANSDUCED CELLS

[75] Inventors: Michael M. Gottesman, Bethesda; Ira Pastan, Potomac, both of Md.; Kazumitsu Ueda

[73] Assignee: National Institutes of Health, Bethesda, Md.

[21] Appl. No.: 454,761

[22] Filed: May 31, 1995

Related U.S. Application Data

[63] Continuation of Ser. No. 416,623, Apr. 4, 1995, abandoned, which is a continuation-in-part of Ser. No. 701,576, May 14, 1991, abandoned, and a continuation-in-part of Ser. No. 202,782, Jun. 3, 1988, abandoned, which is a continuation of Ser. No. 62,583, Jun. 16, 1987, abandoned.

[51] Int. Cl.$^6$ ................................................. C12N 15/63
[52] U.S. Cl. ................. 435/320.1; 435/69.1; 435/172.3; 435/325; 424/93.21; 530/350; 536/23.5
[58] Field of Search ...................... 424/93.21; 435/320.1, 435/69.1, 172.3, 325; 530/350; 935/9, 34, 56, 57, 61, 71; 536/23.5

[56] References Cited

U.S. PATENT DOCUMENTS

| | | | |
|---|---|---|---|
| 4,405,712 | 9/1983 | Vandewoude | 435/5 |
| 4,497,796 | 2/1985 | Salser et al. | 424/93.21 |
| 4,736,866 | 4/1988 | Leder et al. | 800/2 |
| 4,912,039 | 3/1990 | Riordan et al. | 435/69.1 |
| 5,198,344 | 3/1993 | Croop | 435/69.1 |
| 5,206,352 | 4/1993 | Roninson et al. | 536/24.31 |

FOREIGN PATENT DOCUMENTS

| | | |
|---|---|---|
| 85/05629 | 12/1985 | European Pat. Off. . |
| 86/00922 | 2/1986 | European Pat. Off. . |
| 0174810 | 3/1986 | European Pat. Off. . |
| WO 85/05629 | 12/1985 | WIPO . |
| WO 86/00922 | 2/1986 | WIPO . |

OTHER PUBLICATIONS

Marshall ( Aug. 1995) Science:1050–1055, vol. 230.
Ledley (1995) Hum. Gen. Ther. 6:1129–1144.
Roemer et al. (1992) Eur. J. Biochem. 208, 211–225.
Morsy (1993) JAMA, vol. 270, No. 19:2338–2345.
Moritz et al. (1994) J. Clin. Invest., vol. 93:1451–1457.
Ronald Crystal (1995) Science, vol. 270, pp. 404–409.
Stefan Karlsson (1991) Blood, vol. 78, No. 10:2481–2492.
Coghlan (Nov., 1995) New Scientist, vol. 148, pp. 14–15.
Roninso et al., P.N.A.S., vol. 83:4538–4542, Jun. 1986.
Glick et al., Molecular Biotechnology, ASM Press Inc., 1994:45–48.
Gunzburg et al., Molecular Medicine Today, vol. 1, No. 9, pp. 410–417, 1995.
Mastrangelo et al., Seminars in Oncology, vol. 23, 1:4–21, 1996.
Chen et al., *Cell* 47:381 (1986).
Fojo et al., *Proc. Natl. Acad. Sci. USA* 84:265 (1987).
Gros et al., *Nature* 323:728 (1986).
Jaenisch, *Science,* 240:1468 (1988).
Ovejera et al., *Seminars in Oncology* 8 (4) :386 (1981).
Palmiter et al., *Cell* 41:343 (1985).
Ueda et al., *The Journal of Biological Chemistry* 262(2) :505 (1987).
Van Brunt, *Bio/Technology* 6(10) :1149 (1988).
Wilmut et al., *New Scientist,* p. 56 (Jul. 1988).
Clark et al., *Journal of Cellular Biochemistry, Abstracts, UCLA Symposium on Molecular and Cellular Biology, 15th Annual Meetings* (Jan 20–Feb. 15, 1986).
Gros et al., *Cell* 47:371 (1986).
Gros et al., *Proc. Natl. Acad. Sci. USA* 83:337 (1986).
Horio et al., *The Journal of Biological Chemistry* 264(25):14880 (1989).
Ueda et al., *Proc. Natl. Acad. Sci. USA* 84:3004 (1987).
Cornwell et al., *FASEB* 51–54 (1987).
Pastan et al., *New England Journal of Medicine* 316:1388 (1987).

*Primary Examiner*—Christopher S. F. Low
*Assistant Examiner*—Dave Trong Nguyen
*Attorney, Agent, or Firm*—Townsend and Townsend and Crew

[57] ABSTRACT

The present invention provides for vectors carrying a cDNA containing the entire coding region of the human multidrug resistance gene (MDR1) and for a method for introducing MDR1 cDNA into cells thereby inducing a multidrug resistant phenotype.

8 Claims, 2 Drawing Sheets

VECTORS CARRYING MDR1 CDNA WHICH CONFER MULTIDRUG RESISTANCE ON TRANSDUCED CELLS

This is a continuation of application Ser. No. 08/416,623, filed on Apr. 4,1995, abandoned, which is a continuation-in-part of Ser. No. 07/701,576, filed on May 14, 1991, abandoned, and Ser. No. 07/202,782, filed on Jun. 3, 1988, abandoned, which is a continuation of Ser. No. 07/062,583, filed Jun. 16, 1987, abandoned, all of which are herein incorporated by reference for all purposes.

FIELD OF THE INVENTION

The present invention is related to cDNA encoding drug resistance. More particularly, the present invention is related vectors carrying a cDNA containing the entire coding region of the human multidrug resistance gene (MDR1) and methods for introducing MDR1 cDNA into cells thereby inducing a multidrug resistant phenotype.

BACKGROUND OF THE INVENTION

The acquisition of resistance to multiple drugs by tumor cells is a critical problem in cancer therapy. Various multidrug resistant cell lines have been identified and include, for example, rodent cell lines resistant to multiple drugs as well as multidrug resistant (MDR) lines derived from the human KB carcinoma cell line (a HeLa subclone) selected for resistance to either colchicine, vinblastine, or adriamycin which have been extensively studied (see, e.g.,Kartner et al. *Science* 221:1285–1288 (1983), Akiyama et al. *Somatic Cell Mol. Genet.* 11: 117–126 (1985); and Shen et al. *J. Bio. Chem.* 261: 7762–7770 (1986)).

It has been reported that two human DNA sequences designated MDR1 and MDR2, which are homologous to the previously isolated hamster mdr gene (Roninson et al. *Nature,* 309: 626–628 (1984); Gros et al. *Proc. Natl. Acad. Sci. USA,* 83: 337–341 (1986)) are amplified in MDR human KB carcinoma cell lines (Fojo et al. *Proc. Natl. Acad. Sci. USA* 82: 7661–7665 (1985); Roninson et al. *Proc. Natl. Sci. USA* 83: 4538–4542 (1986)). The MDR1 gene encodes a 4.5-kb mRNA which is overexpressed in all of the highly drug-resistant sublines (Roninson et al. supra; Shen et al. *Science,* 232: 643–645 (1986)) and in certain normal and tumor tissues (Fojo et al. *Proc. Natl. Acad. Sci. USA* 84: 265–269 (1987)).

The human MDR1 gene is amplified and expressed in mouse cells transformed to multidrug resistance by genomic DNA from MDR human cells, suggesting that expression of the MDRI gene is responsible for development of the MDR phenotypes (Shen et al. Mol. Cell. Biol. 6: 4039–4044 (1986)). Recent data demonstrates that the cloned mouse mdr gene is sufficient to confer multidrug resistance when introduced into cells in an expression vector (Gros et al. *Nature,* 323: 728–731 (1986). Ueda et al. *J. Biol. Chem.,* 262: 505–508 (1987) and Chen et al. *Cell* 47: 381–389 (1986) have described the isolation of a set of overlapping cDNAs for the entire coding region of the human MDR1 mRNA. However, the construction of a full-length cDNA containing the entire coding region of the human multidrug resistance gene (MDR1) the incorporation of such an MDR1 cDNA into a vector, and the use of such a vector to achieve efficient expression of the cloned gene to confer multidrug resistance in transfected drug-susceptible recipient cells, has not heretofore been disclosed or accomplished.

SUMMARY OF THE INVENTION

The present invention provides for vectors containing a nucleic acid that encodes a full-length MDR1 cDNA. The vectors may be transfected into mammalian (e.g. human) cells where they express a functional human P-glycoprotein. This P-glycoprotein transports various drugs (e.g. Vinca alkaloids, anthracyclines, etc.) that are otherwise toxic out of the host cell and thereby confers on the host cell a multidrug resistant phenotype.

In a preferred embodiment, the present invention provides a vector comprising a full-length human MDR1 cDNA that expresses a functional human P-glycoprotein in a host cell. The host cell may be a mammalian, more preferably a human, and most preferably a drug-sensitive human cell such as a bone marrow cell or a cell of the gastrointestinal tract. The vector is preferably a plasmid or a retrovirus vector. One particularly preferred vector is a retroviral expression vector containing Harvey murine sarcoma virus (Ha-MSV) long terminal repeats (LTRs) bracketing a MDR1 cDNA. One preferred Ha-MSV is the pC01 expression vector. A most preferred vector directs the polarized expression of p-glycoprotein in the host cell.

In another embodiment, the present invention provides for a positive selectable marker comprising a nucleic acid that is a full-length human MDR1 cDNA. Particularly preferred positive selectable markers include any of the above-described vectors.

In still yet another embodiment, the present invention provides for a method of inducing multidrug resistance in mammalian cells. The method includes transfecting the cells with a vector comprising a full-length cDNA for the human MDR1 gene such that the vector expresses a functional human P-glycoprotein. Particularly preferred vectors include any of those described above. The mammalian cells are preferably human cells, more preferably bone marrow cells, embryonic stem cells, or cells of the gastrointestinal tract. The method may additionally comprise monitoring the appearance of the multidrug resistance phenotype in the mammalian cells by screening for sensitivity to drugs against which resistance is desired.

In another embodiment, this invention provides for a method of treating a drug-sensitive disease. The method involves transforming drug sensitive cells of a host to a drug resistant phenotype by transfecting the drug sensitive cells with a vector comprising a full-length cDNA for the human multidrug resistance gene. Then the host is treated with a dose of a drug to which the drug sensitive cells have acquired a drug-resistant phenotype. Preferred vectors for this method include any of the above-described vectors. The drug sensitive cells are preferably human cells and even more preferably bone marrow cells or cells of the gastrointestinal tract.

Finally, in yet another embodiment, this invention provides for a method of introducing heterologous nucleic acids into a cell. The method involves first transfecting the cell with a vector carrying the full length human MDR1 cDNA and with the heterologous nucleic acid and then selecting cells expressing a functional P-glycoprotein along with said heterologous nucleic acid. The vector may be any of the above-described vectors. Preferred cells are human cells more preferably bone marrow cells, embryonic stem cells, or gastrointestinal cells. Where the cell is an embryonic stem cell, the method may additionally involve transplanting that cell back into a developing embryo.

DETAILED DESCRIPTION

The present invention provides for vectors containing the full-length coding region of a human multidrug resistance gene (MDR1). When transfected into a mammalian (e.g. human) host cell these vectors express a 170,000 dalton $M_r$ (molecular weight) membrane glycoprotein (human P-glycoprotein) that produces drug resistance by actively transporting certain cytotoxic agents out of the cells (see Pastan et al., New Eng. J. Med. 316: 1388–1393 (1987) for a review). In particular, the presence of a functional P-glycoprotein confers resistance to Vinca alkaloids, anthracyclines, actinomycin D and some other agents.

Native P-glycoprotein is absent from most normal tissues, but is present in the kidney, the large and small intestine, the liver, the pancreas and the adrenal. In the kidney, intestine, liver and pancreas, the protein is expressed in a polarized manner (Thiebault et al. Proc. Natl. Acad. Sci. USA 84: 7735–7738 (1987)). Thus, it is located on the apical surface of proximal tubule cells in the kidney, on the apical surface of intestinal epithelial cells, on the apical surface of small ductules of the pancreas and on the binary face of hepatocytes. It is situated so that it can transport substrates out of cells and into the lumen of excretory organs. Only on adrenal cells is P-glycoprotein distributed in an apparently non-polarized manner.

It was an unexpected discovery of the present invention that mammalian cells, in particular human cells, when transfected with vectors comprising the full-length human MDR1 cDNA, express a fully functional human P-glycprotein. Even more surprising was the fact that the expressed recombinant protein is expressed in a polarized manner comparable to the native P-glycoprotein.

Transfection of a mammalian cell with the vectors of the present invention results in the transformation of the cell from a drug-sensitive phenotype to a drug-resistant phenotype. Thus, cells which would normally be damaged or killed by certain drugs such as Vinca alkaloids, anthracyclines, etc., are able to tolerate much higher levels of drug exposure with little or no adverse effect. The cells thus acquire a multidrug resistant phenotype comparable to that observed in tumor cells subjected to various chemotherapeutic agents.

Preparation of Full-Length Human MDR1 cDNA

Figure 1:
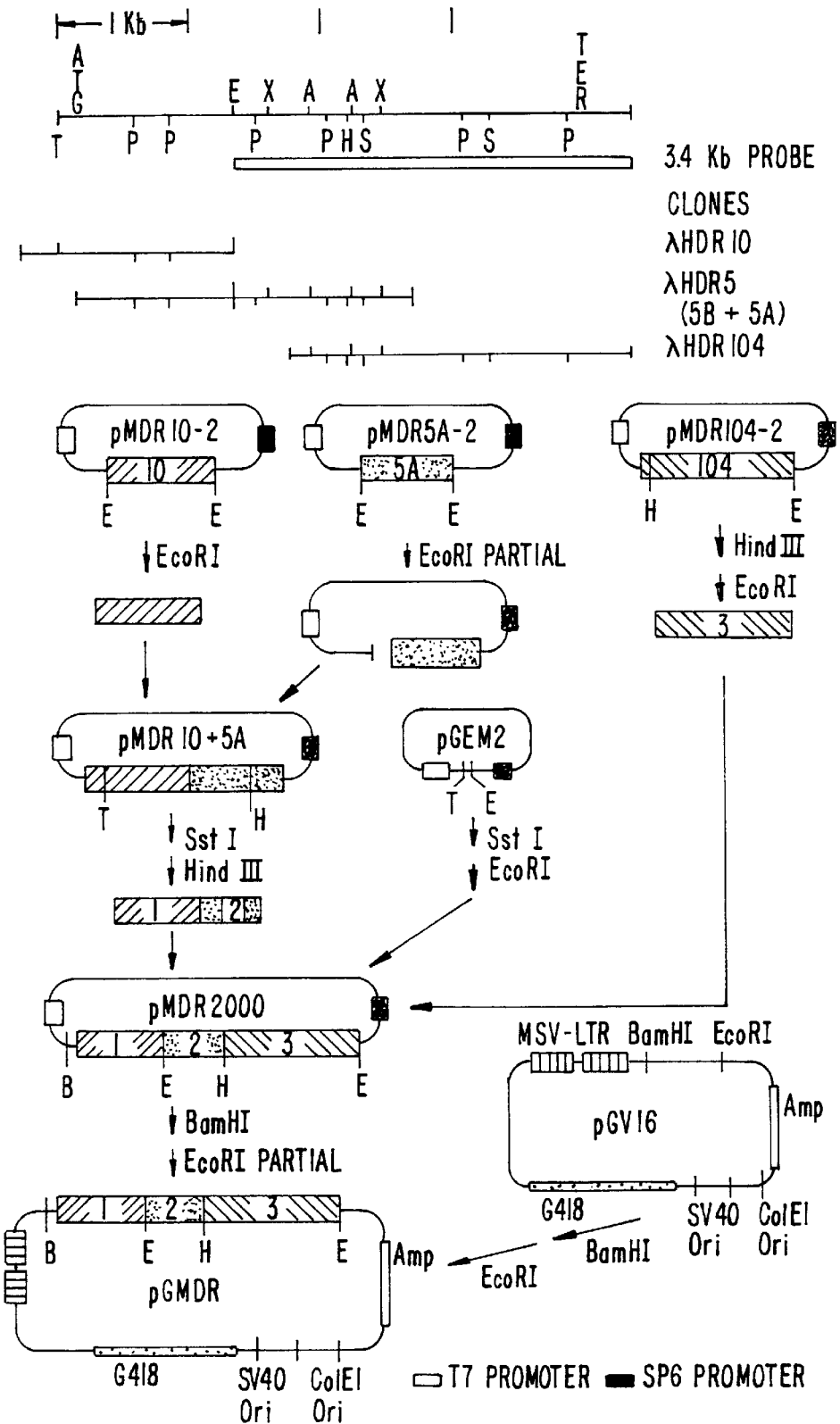
FIG. 1 is a schematic representation of the construction of a full-length cDNA for the human MDR1 gene. The top shows the restriction map of the full-length cDNA for the MDR1 gene and three cDNA overlapping clones isolated from the λgt11 cDNA library made from mRNA from the multidrug-resistant human KB carcinoma mutant line KB-C2.5 which was selected in 2.5 μg/ml colchicine. The bottom shows the reconstruction of a full-length cDNA and its introduction into the mammalian expression vector pGV16. Restriction sites: A, AccI; B, Bam HI; E, EcoR1; H, HindIII; P, PvuII; S, StuI; T, SstI; X, XmnI.

A full-length cDNA for the human MDR1 gene is constructed as described in Example 1 and FIG. 1. Three cDNA clones λHDR5, λHDR10 and λHDR104 provide overlapping nucleic acid sequences that correspond to the full-length human MDR1 cDNA. Briefly, λHDR5 produces two fragments, 5A and 5B, when digested with EcoRI. The 3' fragment (5A) is joined to the an insert from λHDR10 after EcoRI digestion. The resulting construct is then joined to an insert from λHDR104, ultimately producing plasmid pMDR2000 which contains the full-length MDR1 cDNA.

A deposit of the clone containing the entire coding region of the human multidrug resistant gene (pMDR2000) was made at the American Type Culture Collection (ATCC), Rockville, Md. on Apr. 28, 1987, under the accession number 67395. The deposit shall be viably maintained, replacing if it becomes non-viable, for a period of 30 years from the date of the deposit, or for 5 years from the list date of request for a sample of the deposit, whichever is longer, and made available to the public without restriction in accordance with the provisions of the law. The Commissioner of Patents and Trademarks, upon request, shall have access to the deposit.

Because of the large size of the retroviral expression vector and the MDR1 cDNA clones, the above described assembly of the clones into a nucleic acid encoding the full-length MDR1 cDNA is exceedingly difficult. Thus, the assembled pMDR2000 plasmid provided herein is the preferred starting point for the construction of MDR1-containing vectors.

Preparation of Vectors Containing the Full-Length MDR1 cDNA

Using the full-length human MDR1 DNA described above (e.g. plasmid pMDR2000), it is possible to prepare expression vectors containing the full-length MDR1 cDNA using a variety of methods well known to those of ordinary skill in the art. Typical expression vectors contain, at the minimum, a promoter to direct transcription, a ribosome binding site for translational initiation, and a transcription/translation terminator. Preferred vectors include plasmid and phage vectors with retrovirus vectors being most preferred.

While any vector may be used to express the MDR1 cDNA, various vectors differ in the efficiency with which they express the MDR1 cDNA. The relative efficiency of expression of various vectors is illustrated in Table 1 of Example 2. In a particularly preferred embodiment, the full-length human MDR1 cDNA is inserted into the retroviral expression vector pC01 containing two Ha-MSV (Harvey murine sarcoma virus) long terminal repeats (LTRs). While insertion can be accomplished using any convenient restriction sites, the Sac II and Xho I sites of the expression vector are well suited.

Viral lysates are prepared by infection of MDR vector transfected NIH cells with an amphitropic retrovirus. This virus directs the packaging of the MDR1 RNA transcribed from the MDR vector into defective viral particles which are released into the medium. Titers of $10^5$–$10^6$ MDR transforming particles per ml are thus obtained. The construction and packaging of a retroviral expression vector is illustrated in detail in Example 2.

The retroviral vectors carrying the MDR1 cDNA of the present invention can transduce mammalian cells to provide highly efficient introduction of the MDR1 cDNA. For example, the retroviral vectors of the present invention provide highly efficient introduction of the MDR1 gene into NIH 3T3 cells with efficiencies approaching 100% (as compared to 0.1% for DNA-mediated transfection).

Generation of "Model" Cell Lines

The vectors of the present invention may be used in a wide variety of contexts. For example, one goal of chemotherapy research is to find new drugs that either overcome multidrug resistance making current agents more effective or that act not themselves substrates for the efflux pump. To search for such agents it is important to have cell lines that are identical except for their level of P-glycoprotein. The MDR1 vectors of the present invention now make it possible to transduce any drug sensitive cell line of interest, thereby rendering it drug resistant. Thus, for example, the MDR1 vectors of the present invention have been employed to transform colon (HT29), ovarian (OVCAR3) and melanoma (FEMX) cell lines. The resulting drug-resistant cell lines make excellent model systems for the screening therapeutic agents. Thus, in one embodiment, this invention provides for mammalian cells, preferably human cells transfected with a full-length human MDRI cDNA that expresses a functional human P-glycoprotein and confers a multidrug resistant phenotype.

Introduction of the Human Mdr1 Gene into the Bone Marrow

The MDR1 viral vectors of the present invention may be used to transduce bone marrow cells ex vivo resulting in multidrug resistant marrow cells which may be employed to reconstitute marrow in lethally irradiated patients, while still maintaining a chemotherapeutic regimen. Example 8 illustrates the drug resistance of marrow cells in lethally irradiated mice transplanted with MDR1 transduced bone marrow (see Table 4).

Of course, the MDR1 virus of the present invention can be used to transduce any normal cell or tissue in vivo as well, including for example the bone marrow of humans in order to make the transduced cells, tissues or the bone marrow more tolerant to chemotherapeutic agents used in the treatment of cancer or other diseases.

Viral lysates of the human MDR1 gene are prepared either by infection of cell lines carrying the MDR vector with amphitropic retrovirus or by transfection of the MDR vector into cell lines which carry defective virus but which can package virus-like RNAs such as the MDR vector RNA. The latter approach produces lysates of MDR defective viral particles free of non-defective viruses which are better suited for human tests. Human bone marrow, or marrow from appropriate animal subjects is transduced with the MDR viral lysate in vitro, and selected either in vitro, or after re-introduction into the marrow donor, with an appropriate drug. If a marrow-toxic drug is used for selection, the human or animal subject achieves replacement of normal marrow by MDR marrow.

This approach allows more vigorous chemotherapy of tumors and other drug-responsive diseases. The use of the human MDR1 gene expressing a human (as opposed to a murine or other species) cell surface protein (P-glycoprotein), which is the drug efflux pump responsible for the MDR phenotype, allows long-term expression without immune rejection of infected marrow cells. It should be noted that in vivo transformation of drug-susceptible cells to MDR cells is achieved easily by the standard transfection technique.

Introduction of the Human Mdr1 Gene into the Other Tissues

Using a similar approach, MDR1 viral vectors are introduced into the other organs by in vitro or in vivo infection. Such organs are thus transformed to MDR phenotypes and are protected from the toxic effects of chemotherapy. For example, the MDR1 cDNA can be introduced into a non-pathogenic virus with tropism for the gastrointestinal tract. This will protect patients from the gastrointestinal toxicity of such drugs as adriamycin and the like.

Introduction of the MDR1 cDNA into Transgenic Animals

Using MDR constructions in which the actin promoter or another active promoter is linked to the MDR1 cDNA, MDR vector DNA is introduced into the embryonic cells (e.g. ES cells) or oocytes of suitable recipient animals by such techniques as microinjection and the like. Then, by normal growth and development, animals in which the MDR1 cDNA is expressed in various tissues are obtained. It is clear from the foregoing that this methodology allows for raising entirely new, genetically stable, animal lines constitutively resistant to certain selected drugs so that such diseases which otherwise could not be controlled, prevented or treated due to drug toxicity, can now be controlled and treated.

Examples of some drugs which the MDR1 vectors of the present invention can confer resistance to include, but are not limited to, vinblastine, vincristine, VP-16 (etoposide), VM-26 (teniposide), actinomycin D, adriamycin, daunomycin and mithramycin. It is noted that the selection for the drug resistant cell is made by including the drug, against which resistance is desired, in the culture medium.

Somatic Gene Therapy

MDR vector DNA may be used as a cloning vehicle for human genes which are defective in patients with inborn errors of metabolism or in patients whose therapy requires expression of specific gene products. The gene of interest is introduced into the MDR vector under control of a second promoter or is physically linked to the MDR1 gene so as to form a chimeric protein. Viral lysates are prepared as described herein above. Marrow or other tissues infected in vitro or in vivo with such constructions are selected for expression of the MDR1 gene. The linked human gene is expressed in hosts (animal or human) selected with appropriate drugs. Of course, such a procedure can also be employed to introduce selected genes into the germ-line.

In summary, it is clear from the above description that a full-length, cloned human MDR1 cDNA can confer multidrug resistance in the drug-sensitive cells. The present invention allows in vivo transformation of drug-sensitivity to MDR phenotype, making it possible for more effective chemotherapy of drug responsive human diseases which was not heretofore possible.

MDR1 Vectors as Selectable Markers

The identifiable multidrug resistant phenotype resulting from the expression of the MDR1 cDNA and vectors of the present invention provides a positive selectable marker for genetic analysis which can also be used to co-select and co-amplify a second nucleic acid. Because the MDR1 cDNA is a dominant marker, transfection of a host cell results in multidrug resistance. Treatment of a population of cells with a drug to which MDR1 confers resistance (e.g. colchicine) will result in the death of those cells lacking MDR1 and therefore the positive selection of those cells containing MDR1. Where a second nucleic acid is linked to the MDR1 vector, or co-transfected with the MDR1 vector, selection for MDR1 expressing cells will also select for the second nucleic acid.

In addition to providing a dominant selectable marker, the MDR1 cDNA is amplified in drug resistant cells challenged with increasing concentrations of a drug. Association of another nucleic acid with the MDR1 cDNA, as in the vectors of the present invention, allows co-amplification in addition to co-selection of the co-transferred sequence. Such co-selection and co-amplification is demonstrated in Example 4 where the expressed levels of linked MEP increase along with MDR1 when NIH 3T3 cells are challenged with increasing concentrations of colchicine.

Because drug resistance is a dominant marker, it can also be used to introduce passenger genes into bone marrow and other types of cells as an alternative approach to gene therapy. Of course, the MDR1 virus of the present invention can be used to transduce any normal cell or tissue in vivo, including for example the bone marrow of humans in order to make the infected cells, tissues or the bone marrow more tolerant to chemotherapeutic agents used in the treatment of cancer or other diseases.

EXAMPLES

The following examples are offered to illustrate, but not to limit the invention.

Example 1
Construction of a Full-Length MDR1 cDNA

A full-length cDNA for the human MDR1 gene is constructed as shown in FIG. 1. Three cDNA clones λHDR5, λHDR10 and λHDR104 provide overlapping nucleic acid sequences that correspond to the full-length human MDR1 cDNA. Clone λHDR5 is available as two fragments 5A and 5B cloned into pGEM1 at its EcoRI site to give plasmids pHDR51 and pHDR5B which are deposited with the American Type Culture Collection (ATCC) at 12301 Parklawn Drive, Rockville Md. under accession numbers ATCC 67040 and ATCC 67041. Similarly, λHDR10 and λHDR104, cloned into the EcoRI site of pGEM1 to produce pHDR10 and pHDR104 are deposited under accession numbers ATCC 67042 and ATCC 67156.

The insert from λHDR5 is subcloned as two fragments (A and B) after EcoRI digestion. Fragment 5A is the fragment 3' to fragment 5B. Insert 10, prepared from pMDR10-2 is introduced into pMDR5A-2 which is partially digested with EcoRI. Then the SstI-HindIII fragment from pMDR10+5A and the HindIII-EcoRI fragment from pMDR104-2 are inserted into the SstI-EcoRI sites of pGEM2. This step removes the 5'-end EcoRI-SstI non-coding region from fragment 10 producing plasmid pMDR2000. This plasmid was deposited with the ATCC under accession number ATCC 67395.

Example 2
Construction of an Expression Vector Containing MDR1 cDNA

A preferred vector for the efficient transfer of the human MDR1 cDNA into tissue culture or other cells was constructed using a Ha sarcoma virus LTR, as described by Ellis et al., *J. Virol.* 80: 408–420 (1980), and Roop et al., *Nature*, 323: 822–824 (1986).

The construction of a clone comprising the full-length human MDR1 cDNA is described in Example 1. In addition, a deposit of the clone has also been made at the ATCC under accession number 67395. Using the deposited clone, the construction of a retrovirus containing the MDR1 cDNA is achieved by employing standard recombinant methods well known in the art.

In a preferred embodiment, MDR1 cDNA is inserted into the retroviral expression vector pC01 containing two Ha-MSV (Harvey murine sarcoma virus) LTR's using the Sac II and Xho I sites of the pMDR2000 expression vector (FIG. 1).

A 4380 bp Sac I-EcoRI fragment (extending from position −140 to position +4240 of the MDR1 cDNA) was excised from pMDR2000 and inserted into the Sac I-EcoRI site of pGEM2. A Sac II linker was inserted into the Sma I site in the multiple cloning site at the 5' end of the MDR1 insert (this destroys the Sma I site) and an Xho I linker was inserted into the EcoRI site at the 3' end of the MDR1 cDNA insert (the EcoRI site is preserved). The resulting vector, pMDR2000XS, has a unique Sac II site at the 5' end of the cDNA insert and a unique Xho I site at the 3' end of the MDR1 cDNA with Bal 31.

The fragment was excised with Sac I and then blunt-ended with Klenow polymerase. This blunt-ended fragment was inserted with the Pharmacia Universal Translation Terminator (GCTTAATTAATTAAGC) into the Sac I Xho I sites of pMDR2000XS preserving the Xho I site at the 3' end of the cDNA. The sequence at the 3' end of the cDNA was determined by dideoxy sequencing from the SP6 primer and found to delete 286 bases from the 3' noncoding portion of the cDNA, leaving 110 noncoding bases at the 3' end of the cDNA, and no poly A addition signal or poly A tail. The Sac II - Xho I fragment excised from this construction was inserted into the Sac II Xho I sites of the expression vector pC01.

The MDR1 vector DNA, prepared by standard techniques from *E.coli* (e.g. DH5) carrying the MDR vector as a plasmid, was precipitated with $CaPO_4$. The MDR1 vector was then used for transfecting drug-sensitive recipient cells according to standard methods (see, e.g., Shen et al. *Mol. Cell. Biol.* 6: 4039–4045 (1986)).

It should be noted that not all vectors were found to have as high efficiency for the expression of the full length MDR1 as the preferred retroviral vector. Other MDR1 vector constructions using, for example, the actin promoter, have been prepared and can transfect recipient cells to a MDR phenotype, albeit at reduced frequency (for actin, approximately $10^{-5}$).

The first vector into which the full-length MDR1 reconstructed cDNA was cloned, termed pGV16, is shown in FIG. 1. This vector, initially described by Willumsen et al. *Mol. Cell. Biol.* 6: 2545–2654 (1986) has a Maloney leukemia virus LTR and did not efficiently express the MDR1 phenotype. Another vector with a Moloney leukemia virus LTR, pP2, (this vector type is described in Gilboa et al *Biotechniques* 4:504–512, 1986) was also relatively inefficient. Table 1 shows the efficiency of transfection to a colchicine-resistant phenotype of NIH 3T3 cells and by this and other subsequently derived vectors. The third column shows the frequency of

TABLE 1

Figure 2:
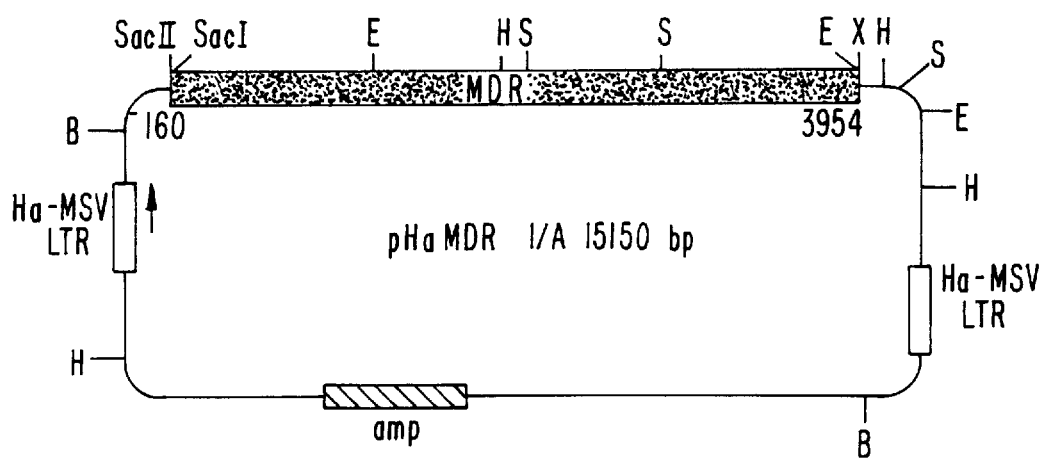
FIG. 2 is a schematic representation of the partial reconstruction map of a preferred expression vector for human MDR1 gene.

| Name of Vector | Source of LTR | Other Factors | Frequency of Colchicine[R]* Colonies One-step | Two-step |
|---|---|---|---|---|
| pGMDR | Moloney leukemia virus pGV16 vector | See FIG. 1 | $<10^{-5}$ | $1 \times 10^{-6}$ |
| pPMDR | Moloney leukemia virus pP2 vector | delete poly A site; no terminator | $5 \times 10^{-6}$ | NT |
| pPMDRT | Moloney leukemia virus pP2 vector | delete poly A site; universal terminator added at 3' end of MDR1 gene | $1 \times 10^{-5}$ | $1 \times 10^{-10}$ |
| pHaMDR | Harvey sarcoma virus pC01 vector | see FIG. 2 with MDR1 poly A site | $1 \times 10^{-3}$ | NT |
| pHaMDR1/A | Harvey/ sarcoma virus pC01 vector | delete poly A site; universal terminator | $2 \times 10^{-3}$ | NT |

*$5 \times 10^{-5}$ NIH 3T3 cells were transfected with 10 μg of MDR1 cDNA. Frequencies are expressed as colchicine resistant colonies per NIH 3T3 cell plated in selective medium. If expressed as colonies per transfected NIH 3T3 cells, frequencies would be approximately 10-fold higher, NT, not tested.

transformation in a single-step experiment directly selecting for colchicine-resistance. The fourth column shows the frequency of selection in a two-step transfection in which the MDR1 vector was first introduced by co-transfection with the $pSV_2neo$ gene with selection for G418-resistance and in a second step G418 resistance colonies were pooled and selected for colchicine resistance.

The results presented in Table 1 clearly indicate that a full-length cDNA encoding MDR1 has not heretofore been prepared and in arriving at the clone of the present invention, various modifications of the vector system had to be made in order to maximize efficient expression, including the use of a retroviral vector with a promoter derived from a Harvey sarcoma virus LTR, and the deletion of the normal MDR1 polyadenylation site.

Example 3

Transfection of Cells After $CaPO_4$-mediated transfection of DNA into human KB cells or mouse NIH 3T3 cells, recipient cells develop a multidrug-resistant phenotype with a frequency of approximately $10^{-3}$ as a result of expression of the human MDR1 cDNA. These frequencies of resistance are comparable to frequencies obtained with other standard dominant selectable markers such as $pSV_2neo$ encoded G418-resistance. MDR recipient cells can be selected, for example, with colchicine and are resistant to vinblastine, adriamycin and actinomycin D, among other drugs. Frequency of drug resistant colonies obtained after transfection of human KB cells is shown in Table 2. The controls are pCO1 with a Harvey ras insert and pCO12 with an EGF receptor insert.

TABLE 2

Frequency of drug resistant colonies

| Plasmid | Colonies per dish | | |
|---|---|---|---|
| | Colchicine | Vinblastine | Adriamycin |
| pHaMDR | 110 | 20 | 30 |
| pCO1 (p21) | 0 | 0 | 0 |
| pCO12 (EGFR) | 0 | 0 | 0 |

K33-1 ($3 \times 10^3$ cells/10 cm) were transfected with 10 µg DNA; 48 hours after transfection, the cells were split into three dishes and cultured with colchicine (10 ng/ml), vinblastine (4 ng/ml) or Adriamycin (30 ng/ml). On day 9, the cells were stained and colonies counted.

Example 4

Use of MDR1 cDNA as a Selectable Marker

The MDR1 cDNA containing vectors of the present invention can also be used to co-select for the expression of other cDNAs and genomic DNAs which are cotransferred with the MDR1 expression vector. For example, the MDR1 vector (pHaMDR) has been cotransferred with cDNAs and genomic DNAs for a protease, termed MEP, the major excreted protein of transformed mouse cells. Colchicine-selected cells expressed the cotransferred MEP genes as demonstrated by immunoprecipitation experiments to detect MEP protein. In the case of uncloned sequences an amplification library was obtained which could be screened or selected for expression of the protein of interest.

The MDR vector can also be used to co-amplify genes which are cotransferred into recipient cells. For example, when NIH 3T3 cells cotransfected with the MDR1 vector and with MEP DNAs were placed in increasing concentrations of colchicine, the recipient cells with amplified MDR1 genes and linked MEP genes were selected. In particular, the MEP gene was co-selected and co-amplified with the MDR1 cDNA. Human MEP proteins were selected by the recipient cells in increasing amounts as the gene was co-amplified with MDR1. Without being bound to any specific theory, it is postulated that the increased production of MEP occurred as a result of co-amplification of the MEP genes with the MDR genes.

Example 5

Packaging the MDR1 cDNA in a Retrovirus

In accordance with the procedures described herein supra, an MDR1 cDNA isolated from a human multidrug-resistant cell line designated C2.5 was placed in a Harvey murine sarcoma virus (Ha-MSV) genome from which the viral oncogene V-$ras^H$ was deleted (FIG. 1). Thus, the MDR1 gene is the only functional eukaryotic gene in this plasmid, which is designated pHaMDR1. The DNA clone was transfected into mouse NIH 3T3 or PA12 cells using the calcium phosphate precipitation technique. PA12 cells contain a defective amphotropic MuLV genome which can package viral transcripts into infectious viral particles. After two days the cells from each 100 mm dish were trypsinized, replated in three 100 mm dishes and incubated with 60 ng/ml colchicine for 10 days. Usually, 50–200 drug-resistant colonies developed from 105 cells transfected with 10 µg pHaMDR1 DNA, whereas no colonies developed in cells transfected with pCO12-EGFR DNA in which an EGF receptor cDNA was inserted in the same position as the MDR1 cDNA in pHaMDR1.

Eight colchicine-resistant clones from PA12 cells were thus isolated, expanded and a 24 hour viral harvest tested for the presence of virus conferring colchicine resistance using mouse NIH 3T3 cells as an indicator cell line. To titrate the virus produced, each clone was grown to confluency and a 24 hour fresh harvest collected. NIH 3T3 cells (or various other cells which could also be used) were plated at $5 \times 10^4$ cells per 60 mm dish in 5 ml of medium (DMEM) containing 10% fetal bovine serum and 2 µg/ml polybrene. Virus dilutions were made in the same medium and 0.5 ml added to each dish of cells. The infected cells were grown for 48 hours, the medium removed, and fresh growth medium containing colchicine or other cytotoxic drugs added at appropriate concentrations. Eight to ten days later, the medium was removed and the colonies stained with 0.5% methylene blue dissolved in 50% methanol.

The clone with the highest viral titer, designated PA12-MDR1, produced $8 \times 10^4$ colchicine-resistant clones per ml. Virus produced by these cells was designated MDR1 virus and used for infecting the ecotropic packing cell line ψ-2. Eight colchicine-resistant ψ-2 cells were isolated and the virus produced by these titered on 3T3 cells. The highest virus titer produced was $2 \times 10^5$ colchicine-resistant cells per ml.

Example 6

Retroviral Induction of Drug Resistance in Cells

To determine if the MDR1 virus could confer resistance to drugs other than colchicine, the amphotropic virus produced by PA12-MDR1 was used to infect human KB cells. Approximately $5 \times 10^4$ KB cells were infected with a $10^{-1}$ dilution of virus. Two days after exposure to virus, the cells were placed in various concentrations of cytotoxic drugs, and nine days later the drug-resistant colonies were stained. The virus conferred resistance to colchicine, vinblastine, VP16 and adriamycin. Other tests showed that similarly infected cells were resistant to puromycin and actinomycin D, but not to cis-platinum. It should be noted that other human cell lines infected with this virus also became multidrug-resistant including the ovarian cell OVCAR-3, the colon carcinoma line HT-29 and the melanoma line FEM-X.

Example 7

Polarized Expression of P-Glycoprotein

As has been mentioned herein above, it has been shown that P-glycoprotein, the product of the MDR1 gene, is expressed in a polarized manner in cells of the colon, small intestine, liver and kidney (Thiebault et al., *Proc. Natl. Acad. Sci. USA* 84: 7735–7738 (1987)). However, it needed to be determined whether this type of polarized distribution on epithelial cells was present in the virus infected cell lines in accordance with the present invention. To establish this, the virus produced by cell line PA12-MDR1 was used to infect dog kidney (MDCK) cells. This line was chosen because the cells form a polarized monolayer in which the cells are intimately connected by tight junctions. MDCK cells were, therefore, infected with the MDR1 virus and clones resistant to colchicine selected. MDCK cells are totally killed by 6 ng/ml colchicine, but to ensure that the background was low, selection was carried out at 12 ng/ml of the drug.

After colchicine selection, live drug resistant MDCK cells were labeled with antibody MRK16 which reacts with an external epitope present on P-glycoprotein (Hamada et al., *Proc. Natl. Acad. Sci. USA*, 83: 7785–7789 (1986)). The intensity of expression of P170 varied greatly. Hence, only those clones that reacted strongly with MRK16 were isolated, expanded and used for further study.

A) MDCK Cell Morphology

MDCK cells assume a polarized morphology when grown on plastic dishes; the cell surface that is exposed to the medium has the same morphologic features as the apical surface of epithelial cells seen in vivo. At confluence, the cells were examined using transmission electron microscopy. Sections taken perpendicular to the plane of the substratum showed that adjacent cells are connected by tight junctional complexes, and the upper cell surface facing the medium has many microvilli. The basal cell surface, the surface facing the substratum, is smoother and occasionally shows deposits of extracellular matrix material next to the plastic substratum (Gaush et al., *Proc. Soc. Exp. Biol. Med.* 122: 931–935 (1966)).

B) Localization of Human P-glycoprotein in pHaMDR-MDCK Cells

MDCK and pHAMDR-MDCK cells were labeled using mouse monoclonal antibody (MRK16) that reacts selectively with P-glycoprotein found in human cells and tumors. To examine upper surface P-glycoprotein expression selectively, cells in 35 mm plastic culture dishes were incubated while still alive at 4° C. with 10 μg/ml MRK16 in Dulbecco's phosphate-buffered saline (PBS) and 2 mg/ml bovine serum albumin (BSA) for 30 minutes, followed by washing at 4° C., and incubation with rhodamine-labeled affinity-purified goat anti-mouse IgG (Jackson ImmunoResearch, Avondale, Pa.) (50 μg/ml, 4° C., 30 minutes) in BSA-PBS. Following washing in PBS at 4° C., the cells were fixed in 3.7% formaldehyde in PBS for 10 minutes at 23° C., and mounted in glycerol.

For examination of surface and/or total cellular P-glycoprotein, cells were primarily fixed in 3.7% formaldehyde in PBS for 10 minutes at 23° C., followed by washing in PBS. In one test designed to detect total cellular P-glycoprotein, the cells were incubated in the same concentrations of primary and secondary antibody described above, except that the antibodies were prepared in a dilutent composed of 4 mg/ml normal goat globulin –0.1% saponin-PBS (without Ca++or Mg++) (NGG-sap-PBS) as described by Willingham et al. in *An Atlas of Immunofluorescence in Cultured Cells*, Academic Press, Orlando, Fla., pp. 1–13 (1985). In another test designed to examine only surface P-glycoprotein, the cells were exposed to antibodies in the absence of saponin. Cells mounted in glycerol were examined using a Zeiss RA microscope equipped with epifluorescence optics and a 4OX, N.A. 1.0, planapochromat objective. Controls included other primary mouse monoclonal antibodies directed at epitopes absent from these cells (nonreactive with either dog or human cells), as well as deletion of the primary antibody step. The specificity of the MRK16 antibody for human P-glycoprotein has already been established as reported by Thiebault et al, *Proc. Natl. Acad. Sci. USA* 84: 7735–7738 (1987) and Willingham et al, *J. Histochem. Cytochem.* 35: 1451–1456 (1987).

When uninfected MDCK cells were examined using MRK16 antibody and immunofluorescence, no specific localization of P-glycoprotein was found, as expected from previous results showing that MRK16 recognizes a human-specific epitope in P-glycoprotein. MDR1-MDCK cells were examined using MRK16 either while alive, or after formaldehyde fixation with or without subsequent saponin permeabilization. These cells showed a strong distribution for human P-glycoprotein in a pattern consistent with a diffuse distribution on their apical plasma membrane, independent of whether saponin permeabilization was used. Since the basal cell surface is inaccessible under these conditions to large proteins in living cells (even though it should be accessible with formaldehyde fixation and saponin permeabilization), nevertheless the distribution of P-glycoprotein on the apical and basal surfaces was determined using electron microscopy.

For ferritin bridge labeling of intact cells, MDCK and pHaMDR-MDCK cells in 35 mm tissue culture dishes were fixed in 3.7% formaldehyde as described for immunofluorescence, and incubated sequentially in accordance with the ferritin bridge labeling method (Willingham, *Histochem. J.* 12: 419–434 (1980)) as follows: (a) MRK16 antibody (10 μg/ml) ; (b) goat antimouse IgG (1:20 dilution of the whole IgG fraction of serum; (c) affinity-purified mouse anti-ferritin (Jackson ImmunoResearch, Avondale, Pa.) (50 μg/ml); and (d) horse spleen ferritin (Sigma) (200 μg/ml). Each of these incubation steps was performed in NGG-sap-PBS for 30 minutes at about 23° C., followed by a wash step in NGG-sap-PBS for 30 minutes at 23° C. The cells were then post-fixed in 2% glutaraldehyde, embedded in situ in Epon 812 and examined at 40 KV using a Philips 400T electron microscope.

Electron microscopy of cells fixed using this formaldehyde fixation, saponin permeabilization and ferritin bridge labeling indicated that P-glycoprotein (P170) was detected mainly on the apical cell surface in MDR1-MDCK cells. No specific localization was found in uninfected MDCK (wild type) cells.

In order to verify the results, a different approach was taken for labeling both cell surfaces. Cells were primarily fixed in glutaraldehyde while still attached to the plastic dish. MRK16 epitope survives this glutaraldehyde fixation step and remains accessible on the cell surface.

Cells were primarily fixed in 2% glutaraldehyde for 15 minutes at 23° C. MRK16 epitope survives this glutaraldehyde fixation step and remains accessible on the cell surface. Following this fixation, the cells were washed in PBS, then scraped from the dish using a rubber scraper. These floating cell sheets were then labeled using the ferritin bridge method as described above, except that the dilutent was BSA-PBS without saponin. The samples were washed at each step by gentle centrifugation. Following this labeling procedure, the fixed cell sheets were then post-fixed in glutaraldehyde and $OsO_4$. The randomly oriented sheets were then embedded as a pellet in Epon and sectioned.

Since the substratum no longer served as a reference, tests were performed to demonstrate that the morphology of the apical and basal cell surfaces were sufficiently different to allow unequivocal identification based on morphology alone. Living cells were labeled at 4° C. with a wheat germ agglutinin-ferritin conjugate (100 μg/ml; E-Y Labs, San Mateo, Calif., USA) to selectively label the apical surface. This lectin conjugate heavily labeled the exposed apical surface, but no label could gain access to the basal surface of the confluent monolayer. The cells were then fixed in glutaraldehyde and scraped, and processed and embedded as a cell pellet.

Examination of these cells in random section revealed that the apical and basal surfaces could be unequivocally identified using morphologic criteria alone. Only labeled apical surfaces showed the numerous microvilli and tight junctions associated with this pole of the cell, while the unlabeled basal surface was smooth, had no tight junctions, and frequently showed deposits of extracellular matrix.

Using these morphologic criteria, the cells were examined by incubating with a cytochemical procedure that demonstrates anionic sites on both the apical and basal surfaces. The anionic surface sites were labeled using the method described by Skutelsky and Bayer, *J. Histochem. and Cytochem.* 35: 1063–1068 (1987), in which fixed scraped cells were incubated in protein-free PBS with poly-L-lysine (100 μg/ml), followed by washing and incubation in ferritin (100 μg/ml) in PBS. The largest component of this labeling method was ferritin, the same large molecule used for the ferritin bridge method for labeling P-glycoprotein. Ferritin, because of its negative charge, binds to the multivalent positively charged polylysine that is attached to negatively charged sites on the cell surface. Both the apical and basal cell surfaces showed heavy labeling with ferritin, thus establishing that the basal surface is fully exposed to large proteins such as ferritin under these conditions.

The cells were then fixed in glutaraldehyde, scraped from the dish, and exposed to MRK16 and the steps of the ferritin bridge method. The ferritin bridge labeling was then quantified as follows: Random samples of cells were photographed at the same magnification, and, the prints were examined using the MacMeasure program (Hook et al. In *Proc. 45th Annual Meeting of Electron Microscopy Society of America* p.920 (1987)) and a MacPlus® computer to measure the linear length of the convoluted plasma membrane on both apical and basal surfaces. This measurement was converted to an estimated surface area assuming a section thickness of 1000Å. The number of ferritin cores in these segments were then counted, and standard errors were derived for the mean of the individual segments examined in each sample.

The apical surface of the cells showed heavy labeling with MRK16, whereas the basal surface showed almost no labeling. These results are quantified and summarized in Table 3. It is clear that P-glycoprotein was distributed selectively on the apical cell surface analogous to the distribution in vivo of P-glycoprotein in the cells of the proximal tubule of the kidney or the bile canalicular surface of hepatocytes.

TABLE 3

Quantitation of Localization of P170 using MRK-16 Antibody and Ferritin Bridge Labeling in pHAMDR-MDCK Cells

| Cell Surface Examined | Ferritin Cores/$\mu^2$ (+/−S.E.) | *Core Counted | Total Area Examined ($\mu^2$) |
|---|---|---|---|
| Apical | 231 (+/−66) | 932 | 3.9 |
| Basal | 29 (+/−8) | 65 | 2.2 |

Normal globulin control samples of pHaMDR-MDCK cells, and uninfected MDCK cells with MRK16, showed background levels of labeling of <10 cores/$\mu^2$ on both apical and basal surfaces. From light microscopic images, the apical surface area of each cell is approximately 2400 $\mu^2$ (including the area of the microvilli). Therefore, for the apical surface of pHaMDR-MDCK cells with 231 cores/$\mu^2$, the apical surface of each cell contains a minimum of $5.5 \times 10^5$ molecules of P-glycoprotein.

The fact that MDCK cells infected with the MDR1 virus also express P-glycoprotein in a polarized manner, suggests that information for polarized expression is located in the structure of the drug transport protein. When the MDCK-MDR1 cell monolayer is disrupted by trypsinization, P-glycoprotein becomes randomly distributed suggesting a portion of the molecule may interact directly or indirectly with an intracellular element which itself is distributed in a polarized manner.

The results presented herein show that infection of cells by a retrovirus containing a full length MDR1 cDNA results in the expression of a functional P-glycoprotein that shows the polarized expression characteristic of a native P-glycoprotein. This expressed P-glycoprotein confers multidrug resistance on the host cells.

When measured for its ability to make NIH 3T3 cells resistant to colchicine, the virus titer was in excess of $2 \times 10^5$ per ml. Evidence that expression of the MDR1 gene alone was sufficient to cause multidrug resistance was strengthened by the observed correlation between the level of drug resistance and the level of MDR1 RNA. A viral titer of $10^5$ obtained using $10^5$ cells for infection is a strong indicator that virtually every cell in a population is made drug resistant by infection with the virus construct of the present invention.

Example 8

Reconstitution of Bone Marrow

The MDR1 virus has also been used to transduce mouse bone marrow cells resulting in multidrug resistant marrow cells which have been employed to reconstitute lethally irradiated mice (Table 4). Briefly, Bone marrow cells were infected by cocultivation of lethally irradiated (22Gy) ψ2-MDR1 producer cells with marrow from femurs of DBA/2J mice. Transfected bone marrow cells were detected as long as 4 weeks after reconstitution of bone marrow in mice treated with colchicine at 20 ng/ml indicating that transfection of bone marrow cells with MDR1 cDNA containing vectors prior to reconstitution provides protection against a chemotherapeutic regimen.

TABLE 4

INFECTION OF MOUSE BONE MARROW WITH THE pHaMDR1 RETROVIRUS

| TREATMENT | PERCENT CFU-GM | |
|---|---|---|
| Prior to Reconstitution | Unifected | Infected |
| No Drug | 100 | 100 |
| Vinblastine, 20 ng/ml | 0 | 7 |
| Colchicine, 20 ng/ml | 0 | 17 |
| 4 Weeks After Reconstitution | | |
| No Drug | 100 | 100 |
| Colchicine, 20 ng/ml | 0 | 2 |

CFU-GM (granulocyte-macrophage colony forming units) were determined using standard culture conditions in semi-solid medium. $10^5$ marrow cells gave approximately 100 CFU-GM.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference.

What is claimed is:

1. A vector comprising a full-length human MDR1 cDNA that expresses a functional human P-glycoprotein in a mammalian host cell wherein expression of said functional human P-glycoprotein renders said host cell multidrug resistant.

2. The vector of claim 1, wherein said vector is a plasmid.

3. The vector of claim 1, wherein said vector is a retrovirus vector.

4. The vector of claim 3, wherein said vector comprises a MDR1 cDNA bracketed by Harvey murine sarcoma virus (Ha-MSV) long terminal repeats (LTRs).

5. The vector of claim 1, wherein said vector, when transfected into an MDCK cell, expresses P-glycoprotein in a polarized distribution in said MDCK cell.

6. A positive selectable marker encoded by a nucleic acid that is a human MDR1 cDNA.

7. The positive selectable marker of claim 6, wherein said marker is a functional P-glycoprotein.

8. The positive selectable marker of claim 6, wherein said marker is encoded by a retroviral vector.

* * * * *